(12) United States Patent
Ahn Jo et al.

(10) Patent No.: US 7,112,569 B2
(45) Date of Patent: Sep. 26, 2006

(54) PROTEIN INHIBITING AGGREGATION OF BETA AMYLOID PEPTIDE

(75) Inventors: Sangmee Ahn Jo, Goyang-si (KR); Inho Jo, Goyang-si (KR); Ho Jeong Kwon, Seoul (KR); Chang Jin Kim, Daejeon (KR); Jeong Eun Park, Seoul (KR)

(73) Assignee: National Institute of Health, (KR)

( * ) Notice: Subject to any disclaimer, the term of this patent is extended or adjusted under 35 U.S.C. 154(b) by 59 days.

(21) Appl. No.: 10/884,729

(22) Filed: Jul. 2, 2004

(65) Prior Publication Data

US 2005/0009749 A1    Jan. 13, 2005

(30) Foreign Application Priority Data

Jul. 11, 2003    (KR) .................... 10-2003-0047199

(51) Int. Cl.
*A61K 38/00* (2006.01)
(52) U.S. Cl. ......................... 514/12; 530/350
(58) Field of Classification Search .................. None
See application file for complete search history.

(56) References Cited

OTHER PUBLICATIONS

Dalakas Pharmacology & Therapeutics 102: 177-193 (2004) "The use of intravenous immunoglobulin in the treatment of autoimmune neuromuscular diseases: evidence-based indications and safety profile".*

Conway et al. Current Pharmaceutical Design 9: 427-447 (2003) "Emerging Beta-Amyloid Therapies for the Treatment of Alzheimer's Disease".*
Hwang, Sung Eun et al., Isolation of Streptomyces SP. KK565 as a Producer of β-Amyloid Aggregation Inhibitor, J. Microbiol. Biotechnol. (2003), 13(5), 809-814.
Klunk, William E. et al., Quantifying Amyloid β-Peptide (Aβ) Aggregation, Analytical Biochemistry 266, 66-76 (1999).
Spungin, Anya et al., Streptomyces Griseus Aminopeptidase Is . . . , Eur. J. Biochem. 183: 471-477 (89).
Iwata, Nobuhise et al., Identification of the Major Aβ 1-42- Degrading . . . , Nature Medicine, vol. 6, No. 2, Feb. 2000.
Eckman, Elizabeth A., Degradation of Alzheimer's . . . , The Journal of Biochemistry, vol. 276, No. 27, Issue of Jul. 6, pp. 24540-24548, 2001.
Zhu, Yinwen Judy et al., Fresh and Nonfibrillar Amyloid β . . . , The EASEB Journal, vol. 14, Jun. 2000: pp. 1244-1254.

* cited by examiner

*Primary Examiner*—Jon Weber
*Assistant Examiner*—Anand Desai
(74) *Attorney, Agent, or Firm*—Lucas & Mercanti, LLP (57) ABSTRACT

The present invention relates to a novel protein inhibiting β amyloid aggregation and a strain producing the protein, more precisely, to a novel protein inhibiting β amyloid aggregation, a gene coding the protein, a *Streptomyces* sp. strain producing the protein and a therapeutic agent for neurodegenerative disorders containing the protein as an effective ingredient. The therapeutic agent of the present invention containing the protein inhibiting β amyloid aggregation as an effective ingredient can be effectively used for the prevention and the treatment of neurodegenerative disorders like Alzheimer's disease.

4 Claims, 7 Drawing Sheets

SEQUENCE LISTING

<160> NUMBER OF SEQ ID NOS: 11

<210> SEQ ID NO 1
<211> LENGTH: 40
<212> TYPE: PRT
<213> ORGANISM: Homo sapiens

```
<400> SEQUENCE: 1

Asp Ala Glu Phe Arg His Asp Ser Gly Tyr Glu Val His His Gln Lys
  1               5                  10                  15

Leu Val Phe Phe Ala Glu Asp Val Gly Ser Asn Lys Gly Ala Ile Ile
                 20                  25                  30

Gly Leu Met Val Gly Gly Val Val
             35              40

<210> SEQ ID NO 2
<211> LENGTH: 11
<212> TYPE: PRT
<213> ORGANISM: homo sapiens

<400> SEQUENCE: 2

Gly Ser Asn Lys Gly Ala Ile Ile Gly Leu Met
  1               5                  10

<210> SEQ ID NO 3
<211> LENGTH: 437
<212> TYPE: PRT
<213> ORGANISM: Streptomyces sp.

<400> SEQUENCE: 3

Met Ser Pro Ser Arg Tyr Arg Ser Leu Ser Ala Ser Ala Leu Ala Val
  1               5                  10                  15

Val Ala Leu Leu Ala Thr Ala Ala Pro Ala Val Gln Ala Ala Pro Ala
                 20                  25                  30

Ser Arg Thr Ala Ala Ala Ala Pro Asp Ile Pro Val Ala Asn Val Lys
             35                  40                  45

Ala His Leu Thr Gln Leu Gln Ser Ile Ala Thr Ala Asn Gly Gly Asn
         50                  55                  60

Arg Ala His Gly Arg Ala Gly Tyr Lys Ala Ser Ile Asp Tyr Val Lys
 65                  70                  75                  80

Ala Lys Leu Asp Ala Ala Gly Tyr Thr Thr Ala Leu Gln Gln Phe Thr
                 85                  90                  95

Ser Gly Gly Ala Thr Gly Tyr Asn Leu Ile Ala Asp Trp Pro Gly Gly
            100                 105                 110

Asp Pro Asn Gln Val Leu Met Ala Gly Ser His Leu Asp Ser Val Thr
        115                 120                 125

Ser Gly Ala Gly Ile Asn Asp Asn Gly Ser Gly Ser Ala Ala Val Leu
    130                 135                 140

Glu Thr Ala Leu Ala Val Ser Arg Ala Gln Leu Thr Pro Asp Lys His
145                 150                 155                 160

Leu Arg Phe Ala Trp Trp Gly Ala Glu Glu Leu Gly Leu Ile Gly Ser
                165                 170                 175

Lys Tyr Tyr Val Asn Asn Leu Gly Ala Thr Glu Arg Ala Lys Leu Asp
            180                 185                 190

Gly Tyr Leu Asn Phe Asp Met Ile Gly Ser Pro Asn Ala Gly Tyr Phe
        195                 200                 205

Val Tyr Asp Asp Asp Pro Val Ile Glu Gln Thr Phe Lys Ser Tyr Phe
    210                 215                 220

Ala Gly Leu Ser Val Pro Thr Glu Ile Glu Thr Glu Gly Asp Gly Arg
225                 230                 235                 240

Ser Asp His Ala Pro Phe Lys Ser Ala Gly Val Pro Val Gly Gly Leu
                245                 250                 255

Phe Thr Gly Ala Ser Asn Thr Lys Ser Ser Ala Gln Ala Gln Lys Trp
```

```
                 260                 265                 270
Gly Gly Thr Ala Gly Gln Ser Phe Asp Arg Cys Tyr His Ser Ser Cys
            275                 280                 285

Asp Asn Thr Ala Asn Ile Asn Asp Thr Ala Leu Asp Arg Asn Ser Asp
        290                 295                 300

Ala Val Ala His Ala Ile Trp Thr Leu Ser Ala Asp Thr Glu Pro Pro
305                 310                 315                 320

Thr Gly Glu Gly Val Phe Ser Ser Thr Thr Asp Val Ala Val Pro Asp
                325                 330                 335

Ala Gly Ser Ala Val Thr Ser Ser Ile Ala Val Thr Gly Arg Thr Gly
            340                 345                 350

Asn Ala Pro Ala Ala Leu Gln Val Gly Val Asp Ile Lys His Thr Trp
        355                 360                 365

Arg Gly Asp Leu Val Val Asp Leu Leu Ala Pro Asp Gly Thr Ala Tyr
        370                 375                 380

Arg Leu Lys Asn Ala Ser Gly Gly Asp Ser Asp Asn Val Ile Ala
385                 390                 395                 400

Thr Tyr Thr Val Asn Ala Ser Ser Glu Thr Ala Asn Gly Thr Trp Lys
                405                 410                 415

Leu Gln Val Arg Asp Thr Ala Ser Gln Asp Thr Gly Phe Ile Asp Ser
            420                 425                 430

Trp Lys Leu Thr Phe
        435

<210> SEQ ID NO 4
<211> LENGTH: 1417
<212> TYPE: DNA
<213> ORGANISM: Streptomyces sp.

<400> SEQUENCE: 4
catcgcaccg ccagctccag gccccggccg tgcacggccg ggtaccccc gcacgttccg      60 tcagtccccg aacggaatcc ggagccttcg atgagcccat cccgctacag atccctgtcc    120
gcgtccgccc tcgccgtcgt ggccctgctc gcgaccgcgg ccccgcggt acaggcggcg     180 cccgcctccc gtacggcggc cgcggcgccc gacatccccg tcgccaacgt caaggcgcac    240
ctcacccagc tccagtcgat cgccaccgcc aacggaggca accgcgccca cggccgggcc    300
ggctacaagg cgtccatcga ctacgtgaag gccaagctgg acgcggccgg atacaccacg    360
gcgctccagc agttcacctc cggcggagcc accgggtaca acctcatagc cgactggccg    420 ggagggggatc cgaaccaggt cctcatggcc ggctcccacc tcgactcggt gacctccggc    480
gccggaatca cgacaacgg ctccggctcg gcagccgtcc tcgagaccgc cctcgcggtc     540
tcccgggcgc agctcactcc cgacaagcac ctgcgcttcg cctggtgggg cgcggaggag    600
ctggggctca tcggctcgaa gtactacgtc aacaacctgg cgccaccga gcgtgccaag     660 ctcgacgggt atctcaactt cgacatgatc ggttcgccca acgccggtta cttcgtctac    720
gacgacgacc cggtcatcga gcagaccttc aagagctact tcgccggtct ctcggtgccc    780
accgagatag agaccgaggg cgacggccgc tccgaccacg ctccgttcaa gagcgcgggc    840
gtgccggtcg gcggcctgtt caccggggcg agcaacacga gtccagcgc ccaggcccag    900 aagtggggcg gcaccgcggg tcagtccttc gaccgctgct accactcgtc gtgcgacaac    960
acggctaaca tcaacgacac tgccctggac cgcaacagcg acgccgtggc ccacgcgatc   1020 tggacccctgt ccgcagatac ggaaccgcc acgggcgagg cgtgttcag cagcaccacg   1080
```

```
gatgtcgccg tcccggacgc agggtcggcg gtcacctcct ccatcgcggt caccggccgg    1140
acaggcaacg ctcccgcggc acttcaggtg ggcgtggaca tcaagcacac ctggcgcggc    1200
gacctcgtcg tcgatctgct ggcgccggac ggcaccgcgt accggctgaa gaacgcgagc    1260
ggcggcgact cggccgacaa cgtgatcgcg acctacaccg tcaacgcgtc gagcgagacc    1320
gcgaacggca cctggaagct ccaggtacgg gacacggcct cgcaggacac cggattcatc    1380
gacagctgga agctcacctt ctgaactcct tcggcgg                             1417
```

<210> SEQ ID NO 5
<211> LENGTH: 7
<212> TYPE: PRT
<213> ORGANISM: Artificial Sequence
<220> FEATURE:
<223> OTHER INFORMATION: AP1 N-terminal peptide

<400> SEQUENCE: 5

Ala Pro Asp Ile Pro Leu Ala
 1               5

<210> SEQ ID NO 6
<211> LENGTH: 21
<212> TYPE: DNA
<213> ORGANISM: Artificial Sequence
<220> FEATURE:
<223> OTHER INFORMATION: degenerative AP1 primer

<400> SEQUENCE: 6
gcgcccgaca taccggtagc c                                              21

<210> SEQ ID NO 7
<211> LENGTH: 6
<212> TYPE: PRT
<213> ORGANISM: Artificial Sequence
<220> FEATURE:
<223> OTHER INFORMATION: AP2 N-terminal peptide

<400> SEQUENCE: 7

Ala Ala Asp Leu Lys Ala
 1               5

<210> SEQ ID NO 8
<211> LENGTH: 21
<212> TYPE: DNA
<213> ORGANISM: Artificial Sequence
<220> FEATURE:
<223> OTHER INFORMATION: degenerative AP2 primer

<400> SEQUENCE: 8
ggcggcgtcc agcttggcct t                                              21

<210> SEQ ID NO 9
<211> LENGTH: 11
<212> TYPE: PRT
<213> ORGANISM: Artificial Sequence
<220> FEATURE:
<223> OTHER INFORMATION: cleavage site of protein

<400> SEQUENCE: 9

Ala Pro Ala Ser Arg Thr Ala Ala Ser Met Ser
 1               5                  10

<210> SEQ ID NO 10
<211> LENGTH: 54
<212> TYPE: PRT

-continued

```
<213> ORGANISM: Artificial Sequence
<220> FEATURE:
<223> OTHER INFORMATION: SCAP

<400> SEQUENCE: 10

Ala Pro Asp Ile Pro Leu Ala Asn Val Lys Ala His Leu Thr Gln Leu
 1               5                  10                  15

Ser Thr Ile Ala Ala Asn Asn Gly Gly Asn Arg Ala His Gly Arg Pro
            20                  25                  30

Gly Tyr Lys Ala Ser Val Asp Tyr Val Lys Ala Lys Leu Asp Ala Ala
        35                  40                  45

Gly Tyr Thr Thr Thr Leu
        50

<210> SEQ ID NO 11
<211> LENGTH: 54
<212> TYPE: PRT
<213> ORGANISM: Artificial Sequence
<220> FEATURE:
<223> OTHER INFORMATION: SCPAP

<400> SEQUENCE: 11

Ala Pro Asp Ile Pro Ile Ala Asn Val Lys Ala His Leu Arg Gln Leu
 1               5                  10                  15

Glu Ser Ile Ala Thr Ala Asn Gly Gly Asn Arg Ala His Gly Arg Ala
            20                  25                  30

Gly Tyr Arg Ala Ser Leu Asp Tyr Met Lys Ala Lys Leu Asp Ala Ala
        35                  40                  45

Gly Phe Thr Thr Arg Val
        50
```

PROTEIN INHIBITING AGGREGATION OF BETA AMYLOID PEPTIDE

This patent application claims the benefit of priority from Korean Patent Application No. 10-2003-0047199 filed Jul. 11, 2003, the contents of which are incorporated herein by reference.

FIELD OF THE INVENTION

The present invention relates to a novel protein inhibiting β amyloid aggregation and a strain producing the protein, more precisely, to a novel protein inhibiting β amyloid aggregation, a gene coding the protein, a *Streptomyces* sp. strain producing the protein and a therapeutic agent for neurodegenerative disorders containing the protein as an effective ingredient.

BACKGROUND

Alzheimer's disease (referred as "AD" hereinafter) is a debilitating neurodegenerative disorder in the elderly effecting millions of individuals throughout the world. One of the pathological hallmarks of AD is the extracellular protein deposits referred as senile plaques (Geula, C. et al., *Nat. Med.*, 4, 827–831 (1998)) that consist predominantly of an aggregated peptide known as β amyloid (referred as "Aβ" hereinafter). Aβ, 39–43 amino acid peptides, is produced through proteolytic processing of the β amyloid precursor protein (referred as "βAPP" hereinafter) by β-secretase and γ-secretase (Glenner, G. G. et al., *Biochim. Biophys. Res. Commun.*, 120, 885–890 (1984); Yasojima, K. et al., *Neurosci. Lett.*, 12, 97–100 (2001)). This peptide is particularly amyloidogenic and appears to form the core of the neuritic plaques. The number of plaques appears to correlate with the degree or severity of the dementia (Hasse, C. et al., *Cell*, 75, 1039–1042 (1993); Selkoe, D. J., *J. Neuropathol. Exp. Neurol.*, 53, 438–447 (1994)). In addition, fibrillar Aβ, amorphous aggregates of Aβ, has been reported to cause neuronal cell death in primary rat hippocampal cultures whereas soluble monomeric species of Aβ are relatively less toxic than fibrillar Aβ (Yankner, B. A. et al., *Science*, 250, 279–282 (1990)). Other studies suggested that prefibrillar aggregates of Aβ are neurotoxic (Zhu, Y. J. et al., *FASEB J.*, 14, 1244–1254 (2000)). Mutations in genes of either APP or presenilins (PS), which seemed to have a γ-secretase activity, may lead to elevation of the production of Aβ, and are associated with severe and early-onset forms of AD (Yoshiike, Y. et al., *J. Biol. Chem.*, 276, 32293–32299 (2001)).

Taken together, Aβ aggregation is considered as a crucial event in the pathogenesis of AD. Accordingly, the efficient inhibition of Aβ aggregation is considered as a powerful way to prevent or treat AD. Therefore, extensive studies have been carried out to discover anti-amyloidogenic compounds from natural or synthetic sources.

Several low molecular weight compounds such as antioxidants, free radical scavengers, cholesterol lowering drugs, calcium channel blockers, and γ-secretase inhibitors have been developed as a therapeutic agent for AD (Selkoe, D. J., *Physiol. Res.*, 81, 741–766 (2001)). Among these compounds, γ-secretase inhibitors are known to decrease Aβ production 30–40% (Schroeter, E. H. et al., *Nature.*, 393, 382–386 (1989); Vandermeeren, M. et al., *Neurosci Lett.*, 27, 145–148 (2001)). Among high molecular weight compounds, anti-Aβ antibody, a macromolecular protein, is a good example to enhance clearing of Aβ deposits in transgenic mice that already had begun to develop plaques, possibly by the recruitment of local microglia (Schenk, D. et al., *Nature*, 400, 173–177 (1999)). Recently, neprilysin which is also known as enkephalinase as well as the common acute lymphoblastic leukemia antigen (CALLA) has been confirmed to be involved in degradation of Aβ-amyloid by its proteolytic activity (Iwata, N. et al., Nat Med., 6, 718–719 (2000); Iwata, N. et al., *Science*, 292, 1550-1552 (2001)). Moreover, reduced neprilysin level in the plaque area of AD brain was found, suggesting that reduced degradation of Aβ caused by low levels of neprilysin may contribute to AD pathogenesis (Yasojima, K. et al., *Neurosci Lett.*, 12, 97–100 (2001)). In addition, Eckman et al. reported recently that endothelin-converting enzyme-1 (ECE-1) degraded Aβ in vitro at multiple sites (Eckman, E. A. et al., *J. Biol. Chem.* 27, 24540–24548 (2001)). These results demonstrate that the endogenous concentration of Aβ peptides is regulated not only by its production but also by its catabolism with a specific proteolytic peptidase. Nevertheless, there is something yet to learn about not only high molecular weight compounds inhibiting neurotoxicity caused by Aβ peptide but also a therapeutic agent for neurodegenerative disorders using a high molecular weight biomolecule without side effects by low molecular weight.

Thus, the present inventors separated a *Streptomyces* sp. strain as a target strain producing an active protein inhibiting the aggregation of Aβ peptide inducing AD, and completed this invention by verifying that a protein separated from the strain could be used as a therapeutic agent for neurodegenerative disorders.

SUMMARY OF THE INVENTION

It is an object of this invention to provide a novel protein inhibiting β amyloid aggregation, a gene coding the protein, a *Streptomyces* sp. strain producing the protein and a therapeutic agent for neurodegenerative disorders containing the protein as an effective ingredient.

DETAILED DESCRIPTION OF PREFERRED EMBODIMENTS

In order to achieve the above object, the present invention provides a novel protein inhibiting Aβ aggregation having an amino acid sequence represented by SEQ. ID. No 3.

The present invention also provides a gene coding the protein.

The present invention further provides a *Streptomyces* sp. strain producing the protein.

The present invention also provides a therapeutic agent for neurodegenerative disorders containing the protein as an effective ingredient.

Hereinafter, the present invention is described in detail.

The present invention provides a novel protein having β amyloid aggregation blocking activity (referred as 'AABA' hereinafter) and an amino acid sequence represented by SEQ. ID. No 3.

Figure 2A:
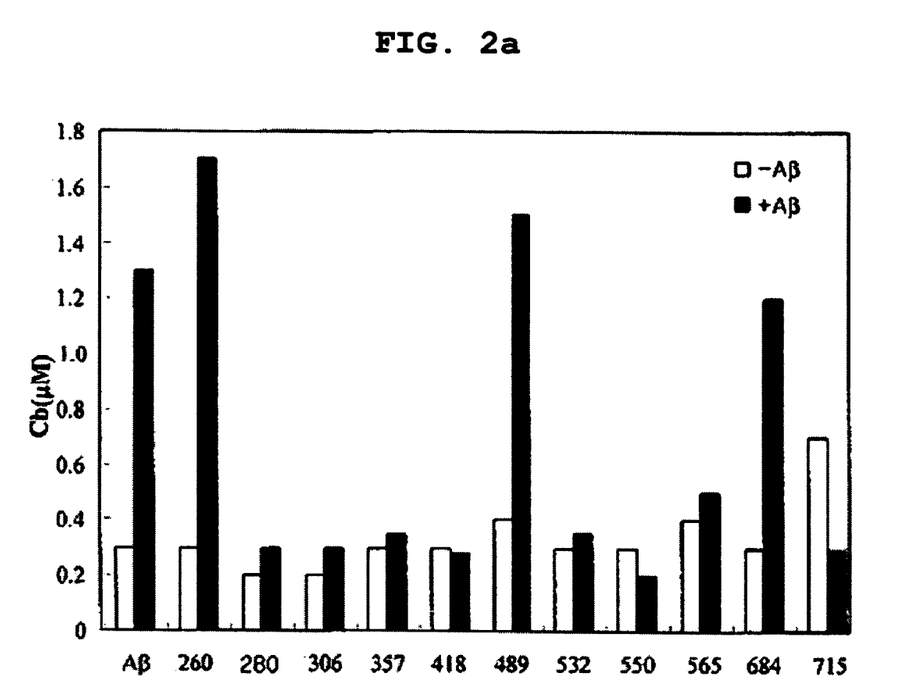
FIG. 2a is a graph showing the effect of microbial metabolites on Aβ1-40 aggregation and fibril formation examined by the Congo red assay.
Figure 2B:
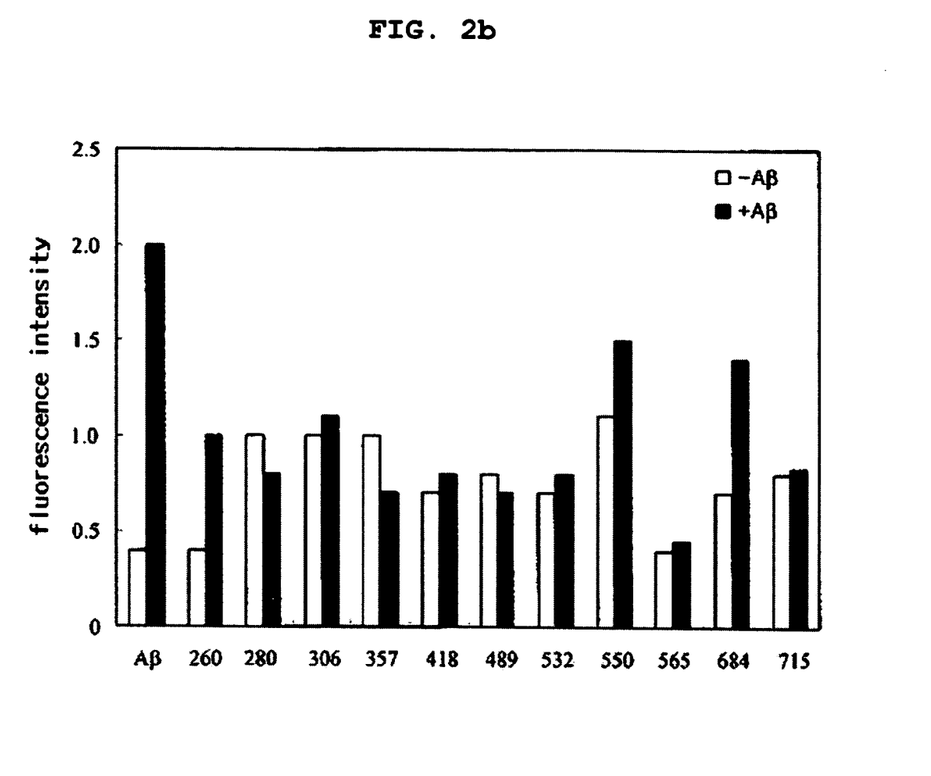
FIG. 2b is a graph showing the effect of microbial metabolites on Aβ1-40 aggregation and fibril formation examined by the thioflavin-T fluorescence assay.

The Aβ aggregation blocking activity of the protein was confirmed by Congo red assay (FIG. 2*a*) and thioflavin T (Th-T) fluorescence assay (FIG. 2*b*). The. protein prevents the neuronal cell death induced by the aggregated Aβ. The molecular weight of the protein of the invention was approximately 45 KDa and base sequence of the protein was identified by IPCR (inverse polymerase chain reaction), based on its cDNA construct. So, the protein of the present invention was confirmed at last to be a protein having an amino acid sequence represented by SEQ. ID. No 3.

The protein of the present invention having an amino acid sequence represented by SEQ. ID. No 3 consists of three major domains, that is ala-rich domain ($11^{th}$–$86^{th}$ amino acid), M20 domain ($132^{nd}$–$192^{nd}$ amino acid) and P domain ($318^{th}$–$410^{th}$ amino acid) M20 domain has an activity of aminopeptidase, and P domain might be involved in intramolecular cleavage taking place in N-terminal of a proprotein. Therefore, the protein of the present invention is expected to have the function of a protease.

The protein of the present invention having AABA is assumed to be an active protein converted from a proprotein that was cut by P domain in front of alanine, the $39^{th}$ amino acid residue of the amino acid sequence represented by SEQ. ID. No 3. The reason for the assumption is that sequence after the $39^{th}$ amino acid residue of the base sequence represented by SEQ. ID. No 3 is equal to base sequence represented by SEQ. ID. No 5 which was confirmed to be N-terminal amino acid sequence of the separated protein. In addition, the $30^{th}$–$38^{th}$ amino acid region (APASRTAAA) of base sequence represented by SEQ. ID. No 3 was also very similar to amino acid sequence represented by SEQ. ID. No 9 (APASRTAASMS), a general cleavage site.

The present invention also provides a gene coding the AABA protein. It is preferred for the gene to have a nucleotide sequence represented by SEQ. ID. No 4. Nucleotide sequence of the gene coding AABA protein represented by SEQ. ID. No 3 is composed of 1404 nucleotides (see SEQ. ID. No 4). The starting codon of the gene coding amino acid of the above protein begins with the $91^{nd}$ nucleotide (ATG). Coding of the above protein is completed at TGA, a termination codon ($1402^{nd}$–$1404^{th}$ nucleotide).

The present invention also provides a *Streptomyces* sp. strain producing the protein. And it is preferred for the strain to be a *Streptomyces* sp. strain KK565 (Accession No: KCCM-10485).

In order to identify a strain producing an Aβ peptide aggregation inhibitor, the present inventors performed screening of microorganism metabolites. As a result, in variety of microorganisms producing compounds and proteins having biological activities were isolated. Among them, a microorganism producing a protein that has the highest Aβ aggregation inhibiting activity was named as KK565.

In order to characterize the above strain KK565, physiochemical characteristics of the strain were examined and taxonomic position thereof was also investigated. Precisely, the strain KK565 forms spores shaping a chain. The spore is spiral and has soft surface. Each spore is shaped like a rod (0.4–0.7×0.8–1.0 um) and non-mobile. The number of spores in a chain is 30–50 or more (see FIG. 3 and Table 1). The KK565 strain grew well in all media tested except inorganic salt-starch and peptone-yeast extract containing agar medium (see Table 2). L-arabinose, D-fructose, raffinose, and D-galactose were utilized by the KK565 strain as a carbon source. The strain has diaminopimelic acid in cell wall verified by the analysis of Becker's method (see Table 3).

From the above results, the present inventors concluded the KK565 strain belongs to a *Streptomyces* species and named it *Streptomyces* sp. KK565. The strain was deposited with the Korean Culture Center of Microorganisms (KCCM), an International Depository Authority, at #361-221. Yurim B/D Hongie-1-dong, Seodaemun-gu, Seould 120-091, Republic of Korea, under Accession NO: KCCM-10485 on Apr. 9, 2003.

The present invention also provides a therapeutic agent for neurodegenerative disorders containing the protein as an effective ingredient. The therapeutic agent of the present invention is preferably used for AD or Down syndrome, but not always limited thereto. The protein of the present invention having an amino acid sequence represented by SEQ. ID. No 3 can inhibit plaque formation or remove plaque deposited already, which is a characteristic cause of neurodegenerative disorders, by inhibiting Aβ peptide aggregation.

The therapeutic agent of the present invention can be administered orally or parenterally and be used in general form of pharmaceutical formulation. The therapeutic agent for neurodegenerative disorders containing AABA protein of the present invention can be prepared for oral or parenteral administration by mixing with generally used fillers, extenders, binders, wetting agents, disintegrating agents, diluents such as surfactant, or excipients.

Solid formulations for oral administration are tablets, pill, dusting powders and capsules. These solid formulations are prepared by mixing with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerinated gelatin, etc.

In general, it has proved advantageous both in human and in veterinary medicine to administer the active compound or compounds according to the present invention in total amounts of about 1~100 mg/kg, preferably 5~50 mg/kg of body weight, one to three times every 24 hours, if appropriate, in the form of several individual doses, to achieve the desired results.

BRIEF DESCRIPTION OF THE DRAWINGS

The application of the preferred embodiments of the present invention is best understood with reference to the accompanying drawings, wherein:

--■-- –Aβ: Reaction mixture in which Aβ1-40 peptide (100 μM) is included,

--o-- +Aβ: Reaction mixture in which Aβ1-40 peptide (100 μM) is not included,

□ –Aβ: Reaction mixture in which only test sample is included (Positive control), ■ +Aβ: Reaction mixture in which Aβ1-40 peptide (100 μM) and test sample are included, Aβ: Control in which test sample is not included, 260~715: Experimental groups having metabolites produced by each strain of the number.

□-Aβ: Reaction mixture in which only test sample is included (Positive control), ■+Aβ: Reaction mixture in which Aβ1-40 peptide (100 μM) and test sample are included, Aβ: Control in which test sample is not included, 260~715: Experimental groups having metabolites produced by each strain of the number, FIG. 4 is a graph showing the effect of heat treatment on the Aβ aggregation blocking activity (AABA) of active compound (SEQ. ID. No 3). The activity was determined by Congo red assay, □ −Aβ: Reaction mixture in which only test sample is included (Positive control), ■ +Aβ: Reaction mixture in which Aβ1-40 peptide (100 μM) and test sample are included, −Aβ/heat: Reaction mixture in which only heated test sample is included, +Aβ/heat: Reaction mixture in which Aβ1-40 peptide (100 μM) and heated sample are included, Aβ(MeOH): Control group in which methanol is used as a test sample, 565-70%: Experimental group in which 70% methanol fraction of a microbial sample (*Streptomyces* sp. KK565) is used.

MeOH: Methanol,

KK565: AABA protein purified from *Streptomyces* sp. KK565 strain,

KK595: Substance purified from *Streptomyces* sp. KK565 strain,

Aβ(1-40): Aβ1-40 peptide (100 μM),

Aβ(25-35): β amyloid 25-35 peptide having an amino acid sequence represented by SEQ. ID. No 2.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Identification of a Strain Producing AABA Protein

In order to identify a strain producing a substance having AABA, the present inventors performed screening of microbial metabolites (Nam, J. Y. et al., *J. Microbiol. Biotech.*, 10, 544–546 (2000); Kwon, H. J. et al., *J. Microbiol. Biotech.*, 11, 1018–1023 (2001)) as follows. As a result, a biological compound and a protein having AABA were separated from in variety of microorganisms.

To investigate the activity of the compound and the protein separated above, the present inventors applied both Congo red method (Klunk, W. E. et al., *J. Histochem. Cytochem.*, 37, 1273–1281 (1989); Klunk, W. E. et al., *Anal. Biochem.*, 266, 66–76 (1999) in which use a dye, Congo red, binding highly with β-s, he-et structure of amyloid presented in the below Example <1-1-1> and thioflavin-T (Th-T) assay (LeVine, H., *Protein Sci.*, 2, 404–410 (1993)) that uses a fluorescent dye, thioflavin-T, binding with fibrous structures presented in the below Example <1-1-2>.

<1-1> Fibrillogenesis Assay

A microorganism library was constructed as follows. About 2,000 microorganisms were cultured on plate media. Some of them were collected from soil in Seoul and Kyunggido, and others were provided by Korea Research Institute of Bioscience and Biotechnology (KRIBB). Each 500 ml Erlenmeyer flask containing 50 ml of medium for stock culture (glucose 2%, yeast extract 0.2%, peptone 0.5%, $KH_3PO_4$ 0.1% and $MgSO_4.7H_2O$ 0.05%) was inoculated with two agar pieces for stock culture of the separated strains. The prepared stock solution was poured in 1 l Erlenmeyer flask containing 150 ml of medium for production (soluble starch 2%, bacto-soytone 0.4%, Phama medium 0.5%, $KH_3PO_4$ 0.1%, $MgSO_4.7H_2O$ 0.05%, NaCl 0.2% and $CaCO_3$ 0.3%). pH of the medium was adjusted to 6.0 with 1 N NaOH and the medium was autoclaved, followed by inoculation of strains. After inoculation, the bacteria were cultured for 5 days and the culture solution was recovered. Centrifugation with the culture solution was performed and supernatant was extracted by methanol. Metabolites were extracted from each microorganism. Among the extracts, a compound or a protein having AABA was hunted.

Aβ peptide (1-40 or 25-35) (QCM, MA, Hopkinton) was dissolved in DMSO as concentrated stock solution (1.68 mM) prior to an experiment and the stock solution was then added to PBS buffer (phosphate buffer saline; 100 mM NaCl, 10 mM $NaH_2PO_4$, pH 7.4). The final concentration of Aβ was 100 μM. The mixed Aβ solution was incubated in the presence or absence of library (Nam, J. Y. et al., *J. Microbiol. Biotech.*, 10, 544–546 (2000)) supernatants at 37° C. for up to 144 hours. The amount of Aβ fibrils remaining intact was measured by the Congo red assay or thioflavin T (Th-T) fluorescence assay as described below.

<1-1-1> Congo Red Assay

Figure 1:
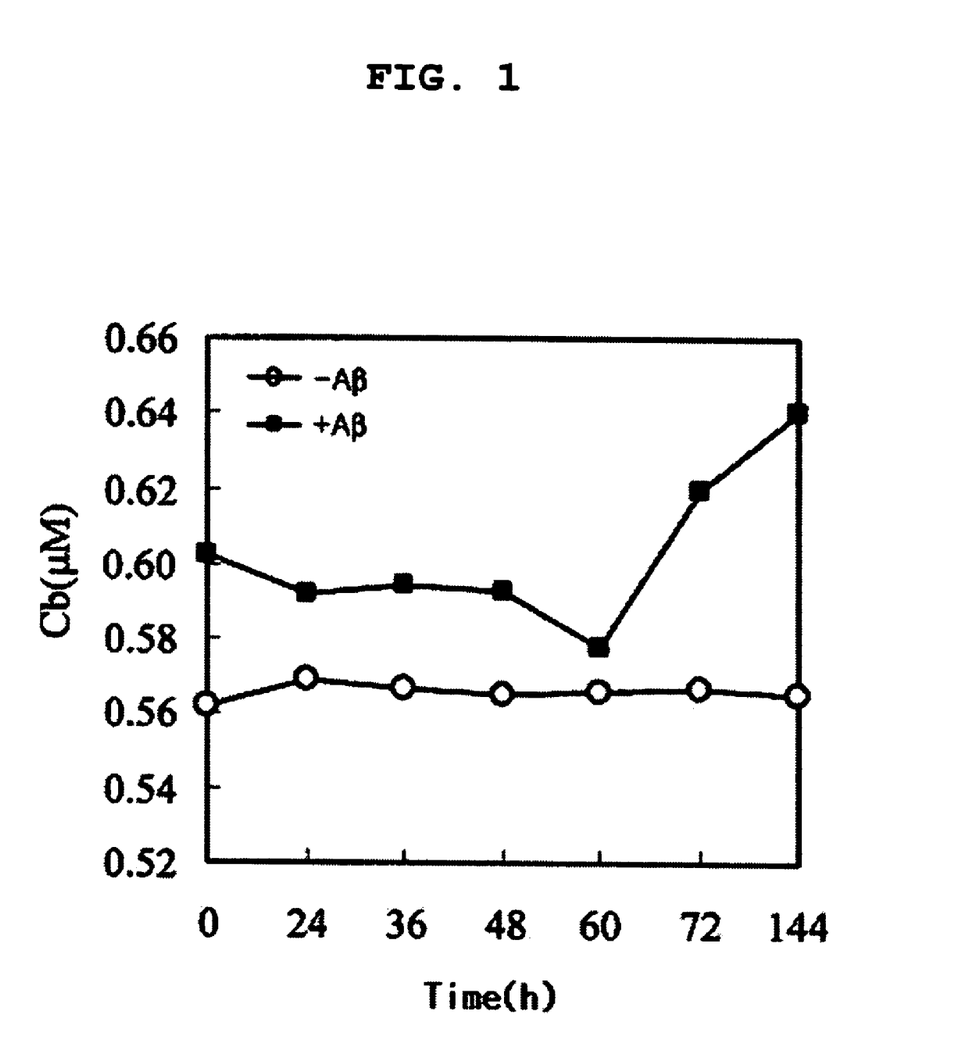
FIG. 1 is a graph showing the time course of aggregation of β amyloid (referred as 'Aβ' hereinafter) 1-40 peptide having an amino acid sequence represented by SEQ. ID. No 1. Aβ aggregation was measured by the Congo red assay.

Congo red assay was used to examine the degree of Aβ aggregation. To determine the optimum condition for readily detectable accumulating level of Aβ aggregates, the present inventors performed a time course experiment of Aβ aggregation at 37° C. FIG. 1 showed the time course of Aβ peptide aggregation at 37° C. without any test agent using Congo red assay. Aβ aggregates were begun to form on day 4 and reached maximum on day 5 or day 6 (FIG. 1).

Thus, the present inventors performed aggregation assay by incubating Aβ routinely for 5 days at 37° C. in this invention. Particularly, Aβ peptide and buffer were incubated for 5 days at 37° C. to allow fibril formation. Congo red was then added to each sample which was incubated for 30 minutes at room temperature. At this point, the optical density (OD) of each sample was measured using a UV spectrophotometer at a wavelength of 540 and 480 nm to assay Congo red binding with Aβ peptide. The quantity of Congo red binding (Cb) Aβ was calculated as follow:

$$Cb[M] = \frac{OD_{540}}{25,295} - \frac{OD_{480}}{46,306}$$

Background signals were determined by measuring the OD of "blank" containing both Aβ and library prior to calculating the total aggregation.

<1-1-2> Thioflavin T Fluorescence Assay

The degree of Aβ-aggregation was determined using fluorescent dye, thioflavin T (Th-T), which specially binds to fibrous structures. First, Aβ peptide stock solution was diluted with 50 mM sodium phosphate buffer, pH 6.0. Th-T was added to each test sample to a final concentration of 10 μM. The activity was measured at an excitation wavelength of 450 nm and an emission of 482 nm that resulted in the optimum detection of bound Th-T. To account for background fluorescence, the fluorescence intensity measured from each control solution without Aβ peptide was subtracted from that of each solution containing Aβ peptide. The fluorescence spectra of Aβ1-40 peptide from different commercial sources and from different lots were in good agreement.

<1–2> Isolation of KK565

To isolate an active compound that has an Aβ aggregation-inhibitory activity, the present inventors applied both Congo red method which uses a dye, Congo red, binding highly with peptide of the Example <1-1-1> or protein aggregation and Th-T assay that uses a fluorescent dye, thioflavin-T, binding with fibrous structures of the Example <1-1-2>. Particularly, Aβ peptide was incubated for 5 days at 37° C. to allow fibril formation as described above. The anti-amyloidogenic activity of libraries was measured by adding 5% cultural broth of microbial libraries prepared in the Example <1-1> into Aβ aggregation solution in 96 well plate. From the 2,000 microbial metabolite libraries, a substance showing AABA activity both in Congo red (93.2% inhibition compared to control) and thioflavin-T (97% inhibition compared to control) was confirmed (FIGS. 2a and 2b). FIG. 2a and FIG. 2b show a part of the metabolite library, in which each number presents the designated number of a strain producing a test sample. The present inventors named a microorganism showing the highest AABA, among the selected microorganisms, KK565.

Example 2

Identification of KK565

The KK565 strain was cultured on a tryptic soy broth (17.0 g pancreatic digest of casein, 3.0 g papaic digest of soybean meal, 5.0 g sodium chloride, 2.5 g dipotassium phosphate, 2.5 g dextrose and 1 l H$_2$O, adjusted to pH 7.3 before autoclaving) for 7 days at 28° C. using a rotary-shaking incubator.

The classification and identification of the cultured KK565 strain was carried out on the basis of ISP (International *Streptomyces* Project) method.

<2-1> Morphological Characteristics

The spore chain morphology of KK565 was examined as follow. The KK565 strain was incubated for 14 days on a yeast extract-malt extract agar (ISP medium 2) (4.0 g yeast extract, 10.0 g malt extract, 4.0 g dextrose, 20.0 g agar and 1 l H$_2$O, adjusted to pH 7.3 before autoclaving). The spore chain morphology of the strain was examined using light and scanning electron microscopy (SEM).

The morphological character of KK565 was investigated by optical and electron microscope using 14 day-cultured cells (Table 1).

TABLE 1

Morphological characteristics of strain KK565

| | |
|---|---|
| Spore surface | Smooth |
| Spore chain morphology | Spiral |
| Spore size | 0.4–0.7 × 0.8–1.0(μm) |
| Spore mobility | None |
| Spore number per chain | >30–50 |

Figure 3:
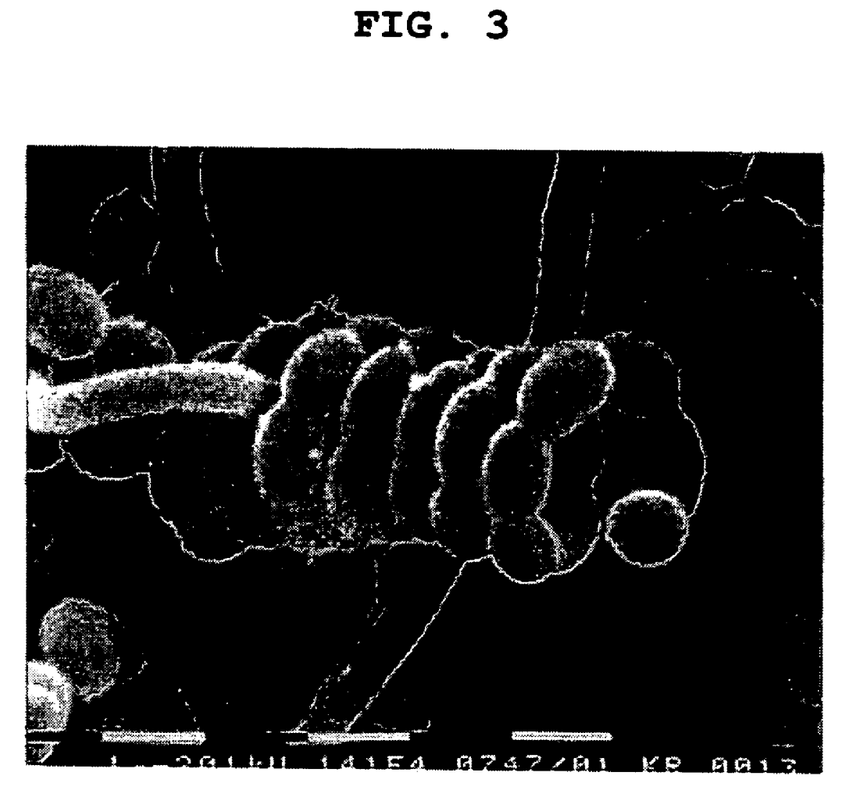
FIG. 3 is a photograph showing the electron scanning morphology of *Streptomyces* sp. KK565 strain of the present invention in SEM (×2300). Bar scale represents 10 μm.

A spore chain showed spiral morphology and the superficies of spore in smooth. The shape of spore was rod with a length, 0.4–0.7×0.8–1.0 μm (FIG. 3).

<2-2> Cultural Characteristics

The cultural character of KK565 was investigated using several ISP media condition with 21 day-cultured cells. The strain grew well in all media tested except inorganic salt-starch and peptone-yeast extract containing agar medium (Table 2).

TABLE 2

Cultural characteristics of KK565

| Media | Growth | Aerial mycelium | Substrate mycelium |
|---|---|---|---|
| Yeast extract-malt extract agar (ISP No. 2) | Good | Gray | Pinkish |
| Oatmeal agar (ISP No. 3) | Good | Gray | Pale Yellow |
| Glycerol-asparagine agar (ISP No. 4) | Moderate | Pinkish Gray | Pale Yellow |
| Inorganic salt-starch agar (ISP No. 5) | Good | White | Pale Yellow |
| Peptone-yeast extract agar (ISP No. 6) | Moderate | Poor | Pale Yellow |
| Tyrosine agar (ISP No. 7) | Good | White | Pale Yellow |
| Glucose-asparagine agar | Good | Gray | Pale Yellow |
| Bennet's agar | Good | White | Pale Yellow |
| Nutrient agar | Moderate | White | Pale Brown |

<2–3> Physiological Characteristics

The possibility of using L-arabinose, D-fructose, raffinose and D-galactose as a carbon source to analyze physiochemical characteristics of KK565 strain was investigated. The type of 2,6-diaminopimelic acid (referred as "DAP" hereinafter), one of cell wall constituents of *Streptomyces* sp. Strain, was also investigated by Becker's method (Becker, B. et al., *Appl. Microbiol.*, 13, 236 (1965)). As a result, it was confirmed based on the analysis of Becker's method that the strain has DAP in cell wall (Table 3).

TABLE 3

Physiological characteristics of KK565

| | | Utilization of C-source | |
|---|---|---|---|
| Starch hydrolysis | + | D-fructose | + |
| Skim milk hydrolysis | − | Galactose | − |
| Nitrate reduction | − | Inositol | + |
| Gelatin liquefaction | − | Mannitol | − |
| Melanin pigment | − | Raffinose | + |
| Soluble pigment | − | Rhamnose | − |
| Milk coagulation | − | Sucrose | − |
| Diaminopimelic acid | LL | D-xylose | + |
| | | D-glucose | − |
| | | L-arabinose | + |
| | | Cellulose | − |

From the above results, the present inventors concluded the KK565 strain belongs to a *Streptomyces* species and named it *Streptomyces* sp. KK565. The strain was deposited at Korean Culture Center of Microorganisms (KCCM), on Apr. 9, 2003 (Accession No: KCCM-10485).

Example 3

Protection of Neuronal Cells from Aβ-Induced Death by AABA Protein Produced by *Streptomyces* sp. KK565

Aβ aggregate is known to induce neuronal cell death as one of its biological activities. Accordingly, KK565 extract could prevent Aβ-induced neuronal cell death if it would block the aggregation of Aβ peptide. To verify this possibility, the present inventors examined the effect of KK565 extract on the viability of neuronal cells treated with Aβ peptide. Cell viability was assessed by a modified 3-(4,5-dimethylthiazol-2-yl)-2,5 diphenyltetrazolium bromide (referred as "MTT" hereinafter).

Particularly, human neuroblastoma cells, SHSY-5Y (American Type Culture Collection, Rockville, Md.), were plated at the density of $2.5 \times 10^4$ in 96 well plates and cultured in the growth media, DMEM/F12 (Gibco BRL) containing 10% fetal calf serum, 2 mM glutamine and 1% penicillin/streptomycin, at 37° C., in the 5% $CO_2$/95% $O_2$ incubator.

Aβ1-40 (100 μM) was prepared under the condition of 100 mM NaCl, 10 mM $NaH_2PO_4$, pH 7.4. Supernatant of KK565 or KK595 (a library strain belongs to *Streptomyces* sp.) culture solution was treated with methanol, resulting in extract. Mixtures containing Aβ1-40 peptide (100 uM) and KK565 or KK595 strain were incubated at 37° C. for 6 days and added into the SHSY-5Y human neuronal cell cultures (final concentration of Aβ: 25 μM). In the meantime, Aβ25-35 (100 μM) was not pre-reacted with the strain extract above before being mixed with SHSY-5Y human neuronal cell culture solution. KK595 showing no Aβ aggregation-inhibitory activity from the Congo red assay was used as a negative control. After incubation for 24 hours, the cells were processed for MTT assay.

MTT assay was performed as follow. The neuronal cells were treated for 24 hours with Aβ (1-40 or 25-35) which had been preincubated with a mixture of compounds for 6 days at 37° C. The cells were rinsed with PBS and then 10 μl of the MTT (0.5 mg/ml) was added. After the incubation for 4 hours, 100 μl of solution containing SDS(10%) and HCl (0.01 N) was added and incubated overnight. On the next day, absorption values of 550 nm were determined with an automatic microtiter plate reader.

Figure 6:
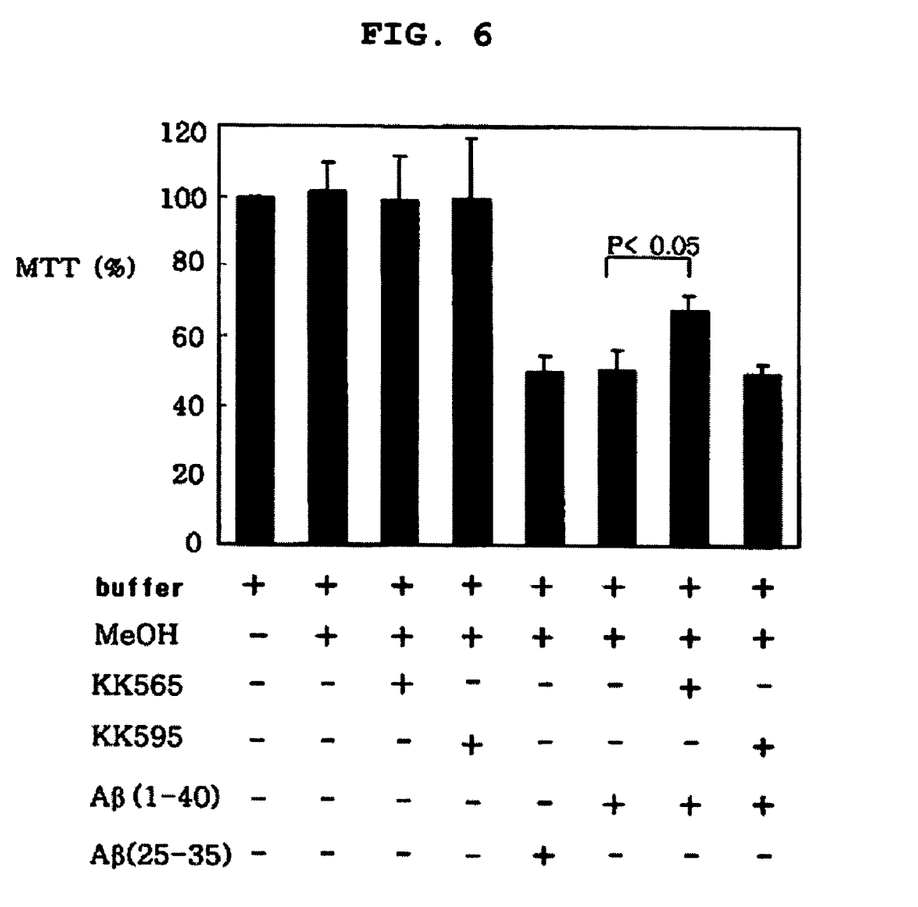
FIG. 6 is a graph showing the protection of neuronal cells from Aβ-induced death by active protein purified from *Streptomyces* sp. KK565 strain (Each bar represents the mean+SEM of three wells).

As a result, it was confirmed that the viability of neuronal cells reduced as much as 50% not only by the treatment of fibrillar Aβ1-40 but also by the treatment of Aβ25-35 (25 μM) (FIG. 6). This result indicates that Aβ25-35 having an amino acid sequence represented by SEQ. ID. No 2 acts as an important factor for Aβ aggregation and the Aβ25-35 peptide motifs are reacted with neuronal cells. KK565 significantly blocked Aβ-induced cell death (cells survived 20% more than those of a control) while KK595, a negative control, did not protect the neuronal cells.

The viability of neuronal cells was not affected at all by the treatment of KK565 alone, suggesting that KK565 has no effect on cell proliferation. These data demonstrate that an active principle of KK565 inhibits the aggregation of Aβ peptide and suggest a possibility that the active principle of KK565 can be developed as a therapeutic agent for neurodegenerative disorders like Alzheimer's disease.

Example 4

Purification and Identification of Anti-amyloidogenic Compound from *Streptomyces* sp. KK565 Culture Broth <4-1> Culture of KK565

The anti-amyloidogenic compound producer, KK565, was grown and maintained at 28° C. on a YS medium plate (soluble starch 10 g/L, yeast extract 2 g/L, agar 20 g/L). For seed cultivation, an agar piece of the stock plate was cut under sterile conditions and incubated into a 500 ml baffle flask containing 50 ml of the culture medium (G.S.S.) (soluble starch 10 g/l, glucose 20 g/l, soy bean meal 25 g/l, yeast extract 4 g/l, NaCl 2 g/l, $K_2HPO_4$ 0.25 g/l, $CaCO_3$ 2 g/l). The pH was adjusted to 7.2 with 1 M NaOH. The flask was cultivated for 48 fours at 28° C. on the rotary shaking incubator (150 rpm) and then the culture broth was transferred to 2 l baffle flasks containing the same medium (400 ml/flask) for large-scale cultivation. All flasks were cultured for 7 days at 28° C.

<4-2> Purification and Identification of Anti-amyloidogenic Compound

Figure 5:
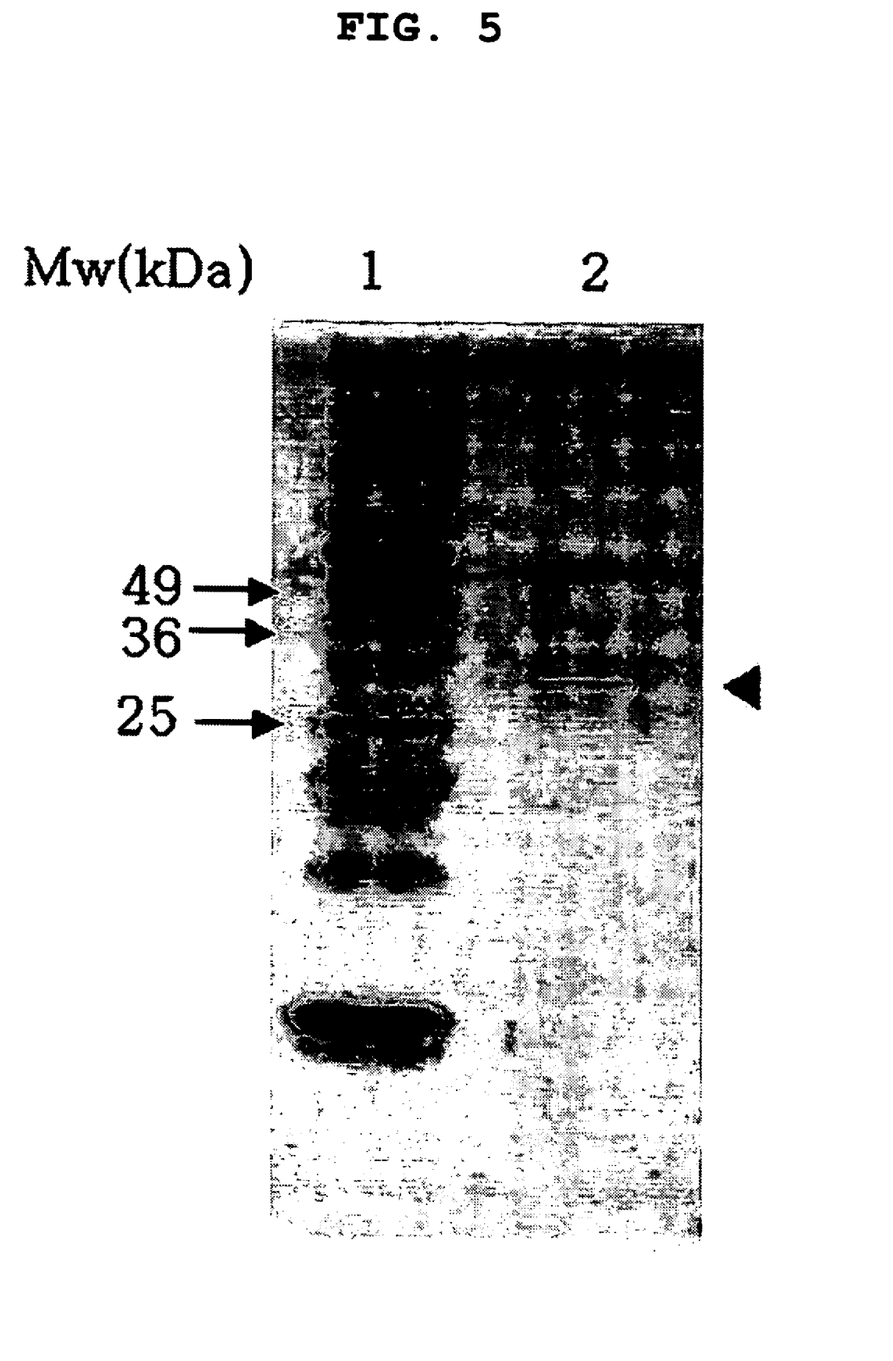
FIG. 5 is a photograph showing the molecular weight of a purified active compound in SDS-PAGE (Arrow indicates the AABA protein), Lane 1: Molecular weight marker, Lane 2: AABA protein purified from *Streptomyces* sp. KK565 strain.

The mycelia were separated from the culture broth by centrifugation (500 rpm, 30 min). The broth was extracted with the same volume of n-butanol and the water-soluble fraction extracted with n-butanol was applied to Diaion HP-20 column. Then, the column was washed with 30% methanol and was eluted with 50%, 70% and 100% methanol in a batch-wise manner. The active 70% ethanol fraction was concentrated in vacuo and then filtered with a MW 10,000 centricon (Vivascience, Germany). The active fractions were concentrated and applied to mono-Q ion exchange column chromatography (Pharmacia, Sweden) for further purification of active compound. Finally, the purity of active compound was confirmed by 12% SDS-polyacrylamide gel electrophoresis (FIG. 5).

The solvent extraction experiment showed that the active compound was not extracted by the treatment of nonpolar solvents such as hexane, chloroform, ethylacetate and n-butanol, suggesting that the active principle would not be a low molecular weight chemical (data not shown). Accordingly, the broth was washed with equal volume of n-butanol to remove the nonpolar, low molecular weight compounds and the water-soluble fraction was used for further purification.

Figure 4:
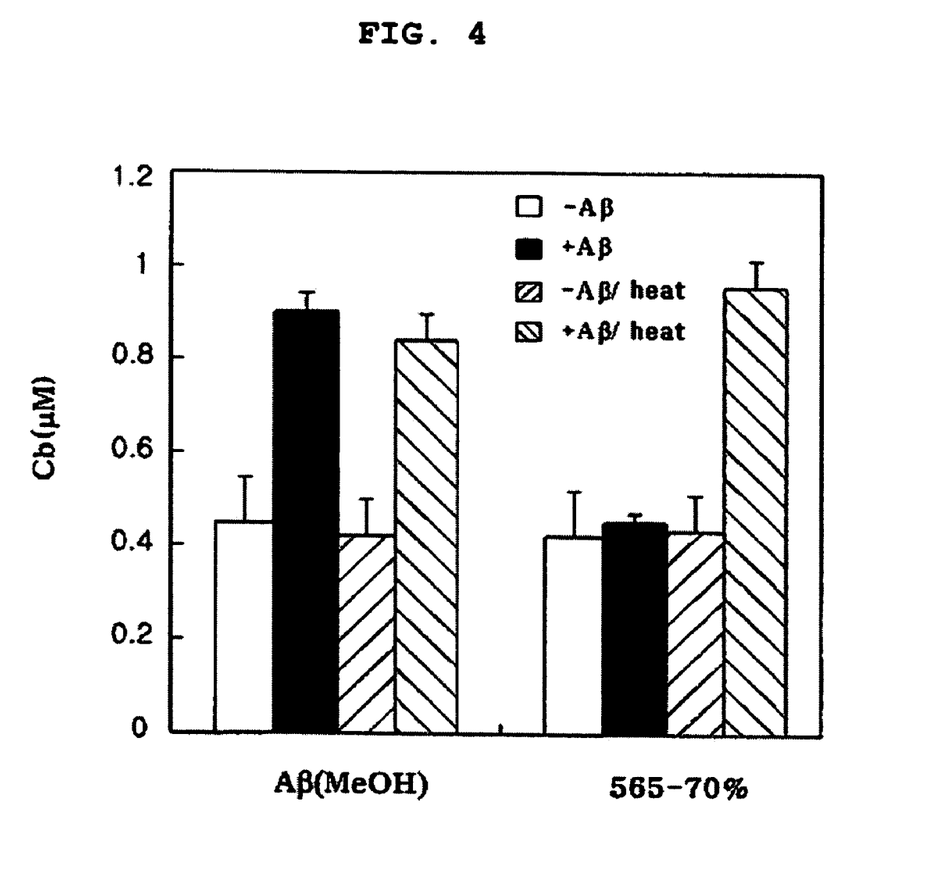

Among the batch-wise eluted fractions of Diaion HP-20 column chromatography, 70% methanol fractions showed the activity. Interestingly, heat-treatment of the fraction for 10 min at 80° C. completely abolished the activity, suggesting that the active compound would be a protein or a peptide (FIG. 4). From MALDI-TOE mass analysis of 70% methanol fractions, the present inventors confirmed that the active compound of KK565 was a protein. To verify the result again, electrophoresis was performed to separate bands. Then, amino acid of N-terminal of the band was examined, resulting in the confirmation that the active compound of the strain was a protein.

The 70% methanol fractions were concentrated and further separated with Centricon (MW 10,000) to cut off the residual low molecular weight compounds. The active fraction having more than molecular weight 10,000 was purified with mono-Q column and the fractions were separated under SDS-polyacrylamide gel electrophoresis. As a result, an active compound was separated as a major band (referred as band 'A' hereinafter) with molecular weight approximately 30 kDa together with a weak band (referred as band 'B' hereinafter) having over 30 kDa molecular weight (approximately 45–50 kDa) (FIG. 5). The band 'A' was extracted to analyze sequence of terminal region of amino group. As a result, it seemed to be a peptide represented by SEQ. ID. No 5 and SEQ. ID. No 7. Among nucleotide sequences that are coding amino acid sequences represented by SEQ. ID. No 5 and No 7, degenerative DNA sequences represented by SEQ. ID. No 6 and No 8 were selected based on the frequency of codon utility for PCR.

Degenerative DNA sequences were drawn, followed by PCR. Particularly, a nucleotide sequence coding a peptide sequence composed of 7 amino acids that were confirmed by sequence analysis of N-terminal amino acid of a separated/purified protein was put in a database, followed by NCBI blast searching. As a result, it was confirmed that the proteins coded by the above nucleotide sequence were corresponding to *Streptomyces griseus* aminopeptidase (SGAP; see SEQ. ID. No 10; Spungin, A. and Blumgerg, S., *Eur. J. Biochem.*, 183, 471–477 (1989)) and *S. coelicobr* putative aminopeptidase (SCPAP; see SEQ. ID. No 11). Amino acid sequences of AABA protein of the present invention and the two proteins confirmed by the above examination were aligned to compare amino acid sequences, resulting in the confirmation that two amino acid sequences represented by SEQ. ID. No 5 and No 7 were common. Finally, degenerative sequences (SEQ. ID. No 6 and No 8) coding the two common amino acid sequences were prepared, which would be used as primers for PCR. IPCR was performed again by using the PCR product as a primer. Particularly, PCR was performed by using amino acid sequences represented by SEQ. ID. No 6 and No 8 as primers as follows; predenaturation at 95° C. for 3 minutes, denaturation at 95° C. for 20 seconds, annealing at 60° C. for 40 minutes, polymerization at 68° C. for 5 minutes, 30 cycles from denaturation to polymerization, and final extension at 72° C. for 10 minutes.

"IPCR (inverse PCR)" is a gene amplification technique that amplifies a DNA region close to the well-informed sequences of genomic DNA, which takes advantage of circular DNA changed from a genomic DNA fragment of KK565 strain. Particularly, genomic DNA of KK565 was digested with BamHI, EcORI, and TaqI, followed by PCR with samples obtained from self-ligation by using a primer prepared from the amplified template DNA fragments, which were also obtained by PCR, to identify nucleotide sequence of a sample DNA. IPCR was then performed with the resultant sequence, amplified by PCR above, using a proper primer, which was repeated to amplify whole sequence of a gene coding AABA protein in order to confirm both initiation codon and termination codon of AABA protein. Genes of AABA protein were cloned from the whole sequence disclosed above and the nucleotide sequences were identified.

As a result, it was confirmed that a gene coding AABA protein of the present invention had a nucleotide sequence represented by SEQ. ID. No 4. From the analysis of base sequences of the gene, the present inventors also confirmed that an active protein of the invention had an amino acid sequence represented by SEQ. ID. No 3 comprising 437 amino acids (protein of band B). Further, a protein corresponding to band A was proved to be a fragment of a protein corresponding to band B. The amino acid sequence represented by SEQ. ID. No 3 was compared with any other listed in NCBI database by blast search. As a result, it had 87% homology with *Streptomyces griseus* sp. aminopeptidase. Therefore, the active protein of the present invention is a novel protein whose amino acid sequence and its DNA sequence were not listed in NCBI database, yet.

INDUSTRIAL APPLICABILITY

As explained hereinbefore, a protein inhibiting Aβ aggregation, which is separated from *Streptomyces* sp. KK565, can be effectively used for the prevention and the treatment of neurodegenerative disorders including Alzheimer's disease. In addition, the protein can be a good tool for identifying homologues in mammals and the study of biochemical and cytological functions of the protein enables explaining the molecular mechanism of Aβ accumulation in brain.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated β-amyloid aggregation inhibiting protein comprising the amino acid sequence of SEQ. ID. NO: 3.

2. A therapeutic agent comprising the isolated protein of claim 1 as an effective ingredient for the inhibition of Aβ aggregation for in vitro cell culture assays.

3. The isolated protein according to claim 1, wherein is encoded by a polynucleotide comprising the nucleotide sequence of SEQ. ID. NO: 4.

4. The isolated protein according to claim 1, which is isolated from *Streptomyces* sp. KK565 deposited under Accesion NO: KCCM-10485.

* * * * *